United States Patent [19]

Hawkins

[11] Patent Number: 5,018,533
[45] Date of Patent: May 28, 1991

[54] APPARATUS FOR THE REDUCTION OF APNAA IN THE EDENTULOUS

[76] Inventor: Richard H. Hawkins, 1245 Broad Ave., Gulfport, Miss. 39501

[21] Appl. No.: 357,553

[22] Filed: May 25, 1989

[51] Int. Cl.⁵ ............................................. A61C 7/08
[52] U.S. Cl. .................................. 128/848; 128/859; 128/861
[58] Field of Search .................... 128/848, 859–863; 433/6, 7, 140, 171

[56] References Cited

U.S. PATENT DOCUMENTS

| | | | |
|---|---|---|---|
| 2,659,366 | 11/1953 | Savarese | 128/861 |
| 2,669,988 | 2/1954 | Carpenter | 128/861 |
| 2,966,908 | 1/1961 | Cathcart et al. | 128/861 |
| 3,126,002 | 3/1964 | Owens | 128/861 |
| 3,312,216 | 4/1967 | Wallshein | 433/6 X |
| 3,513,838 | 5/1970 | Foderick et al. | 128/861 |
| 3,536,069 | 10/1970 | Gores | 128/861 |
| 4,304,227 | 12/1981 | Samelson | 128/848 |
| 4,553,549 | 11/1985 | Pope et al. | 433/6 X |
| 4,593,686 | 6/1986 | Lloyd et al. | 128/848 |
| 4,676,240 | 6/1987 | Gardy | 128/848 |
| 4,715,368 | 12/1987 | George | 433/6 X |
| 4,901,737 | 2/1990 | Toone | 128/861 X |

FOREIGN PATENT DOCUMENTS 312368  4/1989  European Pat. Off. ............ 128/848

*Primary Examiner*—Robert A. Hafer
*Assistant Examiner*—Kevin G. Rooney
*Attorney, Agent, or Firm*—Alexander Norcross

[57] ABSTRACT

A process for reducing the occurrence of apneic episodes in an edentulous person including the steps of determining a neuromuscularly balanced position of the temporal mandibular joint of the edentulous person and shaping an oral appliance to maintain the neuromuscularly balanced position during sleep. The oral appliance has upper and lower plates with opposing planar rest surfaces which maintain the jaw position and angle corresponding to the neuromuscularly balanced position.

1 Claim, 3 Drawing Sheets

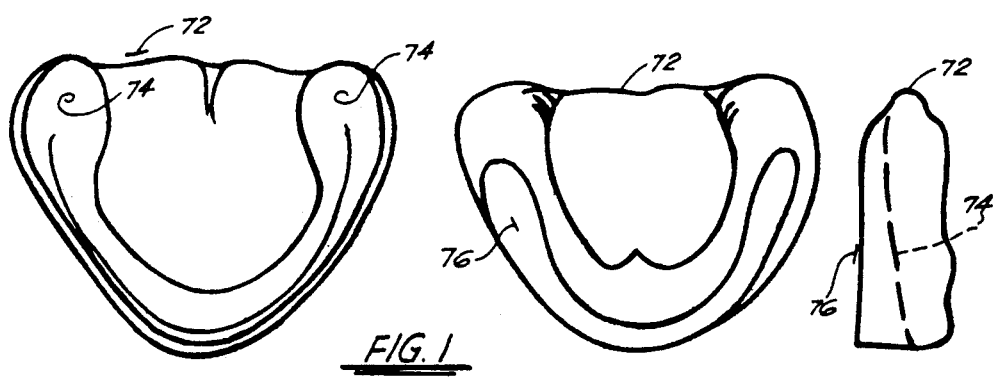
FIG. 1    FIG. 2    FIG. 3
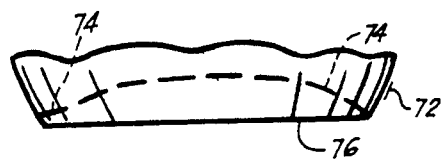
FIG. 4
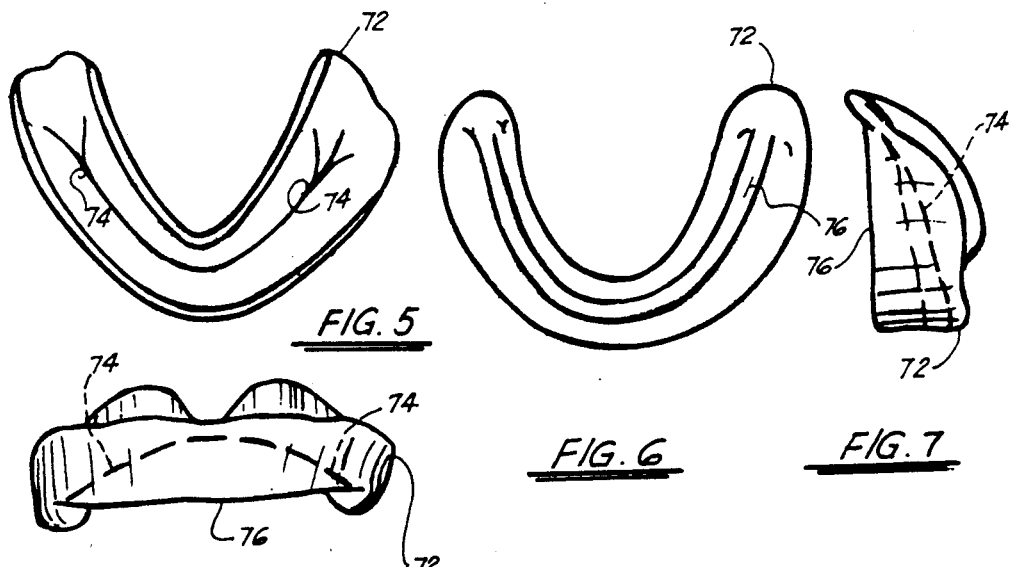
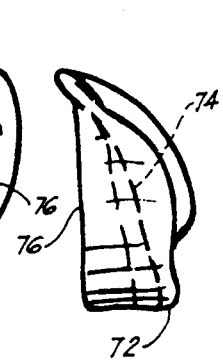
FIG. 5    FIG. 6    FIG. 7
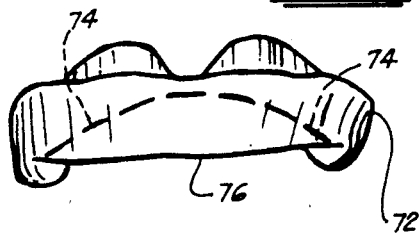
FIG. 8

5,018,533

APPARATUS FOR THE REDUCTION OF APNAA IN THE EDENTULOUS

BACKGROUND OF THE INVENTION

It has recently been suggested that some forty to fifty percent of the population over age fifty years experience a sleep disorder breathing. About five percent of the general adult population, and ten percent of men over the age of forty years, may have clinically important sleep apnea. This is now recognized as a cause of considerable morbidity and, potentially, sudden death.

Such sleep disorder breathing frequently goes undiagnosed. The most common symptom presented is excessive daytime sleepiness, and such symptoms and behavioral patterns are often overlooked or considered as normal sequela of aging.

In addition, disordered sleep of the institutionalized elderly is often treated with strong drug therapy, including the administration of hypnotics and sedatives. These drugs are frequently used because disordered sleep may produce sleep onset insomnia or frequent early morning arousals with resulting poor sleep maintenance. Paradoxically, this drug treatment worsens the quality of sleep and increases the risk of obstructive apnea. This initiates a vicious cycle in which further deterioration of sleep results in increased use of the drugs until such heavy sedation occurs that confusion or dementia results.

Where sleep apnea has been properly diagnosed, surgery has been considered the only reliable treatment, with tracheostomy being the surgical intervention against which other treatments are measured.

Some attempts have been made to create noninvasive devices for reducing apnea. One such is the "equalizer" a commercially designed and available mouth insert having tubes extending outward between the lips, claimed to reduce air pressure from the nasal passages.

This device is an embodiment of U.S. Pat. No. 4,553,549 to Pope and Hawkins (the applicant here) which discloses an oral appliance for maintaining mandible in a neuromuscularly balanced rest position, together with tubes for providing equalization of air pressure from within the oralpharyngeal cavity to the outside air.

The standard treatments for Sleep Disorders in the Elderly remains as described in Michael G. Moran, M.D., et al, "Sleep Disorders in the Elderly", *American Journal of Psychiatry* 145, Nov. 11, 1988.

SUMMARY OF THE INVENTION

This invention concerns a specific oral orthopedic appliance, designed for correcting neuromuscular imbalance and a process for applying the same to provide effective treatment for sleep apnea in the elderly edentulous patient, avoiding the more invasive treatments of tracheostomy and uvulopalatopharyngeoplasty (UPPP), both of which have attendant non-beneficial side effects and risks.

The inventive neuromuscular oral appliance prevents overclosure of the mandible, common in the edentulous human. It maintains the normal tonus of the musculature which elevates and depresses the mandible; in addition, the superior genial tubercles are advanced (along with the anterior portion of the mandible) and, since these serve as attachments of the genioglossus muscle, the tongue is held forward. This, in turn, increases the posterior air space. The apparatus also elevates the hyoid bone, decreasing the distance between the mandibular plane and the superior aspect of the hyoid, producing a favorable change for diminishing apneic episodes.

The apparatus also increases the oral volume, permitting the tongue to function normally, reducing its tendency to be forced posterially into the oropharynx.

A low frequency TENS device is used to activate the facial and trigeminal nerve in order to gain accurate, muscle trimmed impressions of the upper and lower jaws upon which the appliance is seated, following the technique documented by, for example, Jankelson, Bernard, et al, *Neuromuscular Clinical Techniques for Maximum Functional and Aesthetic Rehabilitation of the Edentulous Patient, Myotronics Research, Inc.*, undated. The technique assures that the resting position of the mandible will be physiologically neutral in three planes of space.

It is thus an object of this invention to show an apparatus which decreases the occurrence of sleep apnea in the edentulous elderly.

It is a further object of this invention to disclose an apparatus which more properly positions the mandible and the tongue in a sleeping, edentulous person.

It is a further object of this invention to disclose an apparatus which increases the oral volume within a sleeping edentulous human.

It is a further object of this invention to show an apparatus which increases the posterior air space within a sleeping edentulous human.

These and other objects of the invention can be more clearly seen from the detailed description of the preferred embodiment.

BRIEF DESCRIPTION OF THE DRAWINGS

FIG. 1 is a top view of a top plate of the invention.

FIG. 2 is a bottom, inner view of the apparatus of the invention.

FIG. 3 is a side view of the top plate of the apparatus of the invention.

FIG. 4 is a frontal view of the top plate of the apparatus of the invention.

FIG. 5 is a bottom view of the bottom plate of the apparatus of the invention.

FIG. 6 is a top, inner view of the bottom plate of the apparatus of the invention.

FIG. 7 is a side view of the bottom plate of the apparatus of the invention.

FIG. 8 is a frontal view of the bottom plate of the apparatus of the invention.

DETAILED DESCRIPTION OF THE PREFERRED EMBODIMENT

Figure 9:
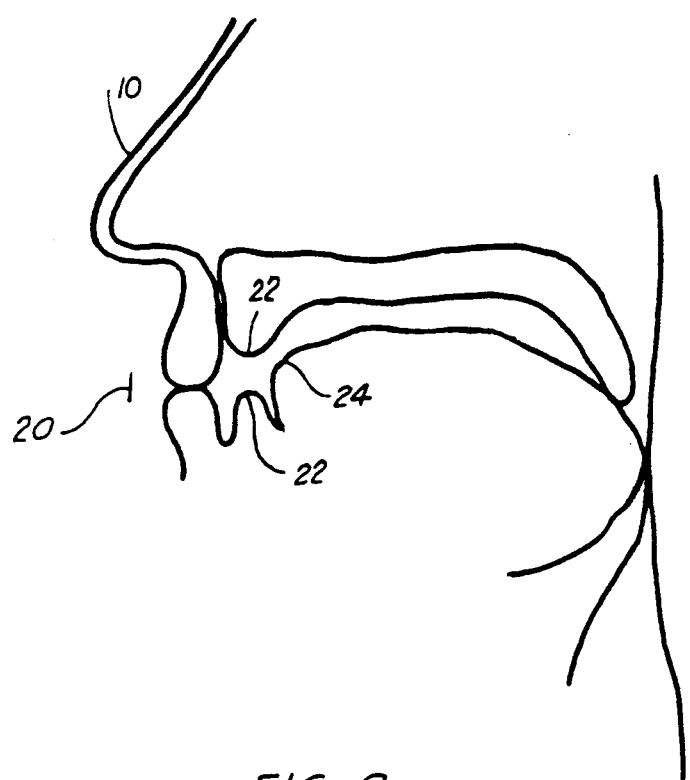
FIG. 9 is a side view showing the mandibular position of an ordinary, non-edentulous human.
Figure 10:
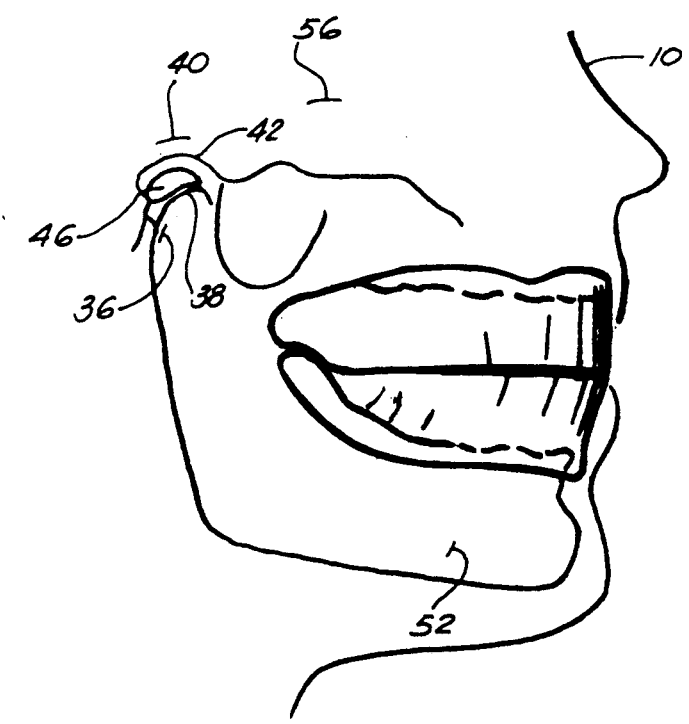
FIG. 10 is a side view of an edentulous human with the apparatus in question installed.
Figure 11:
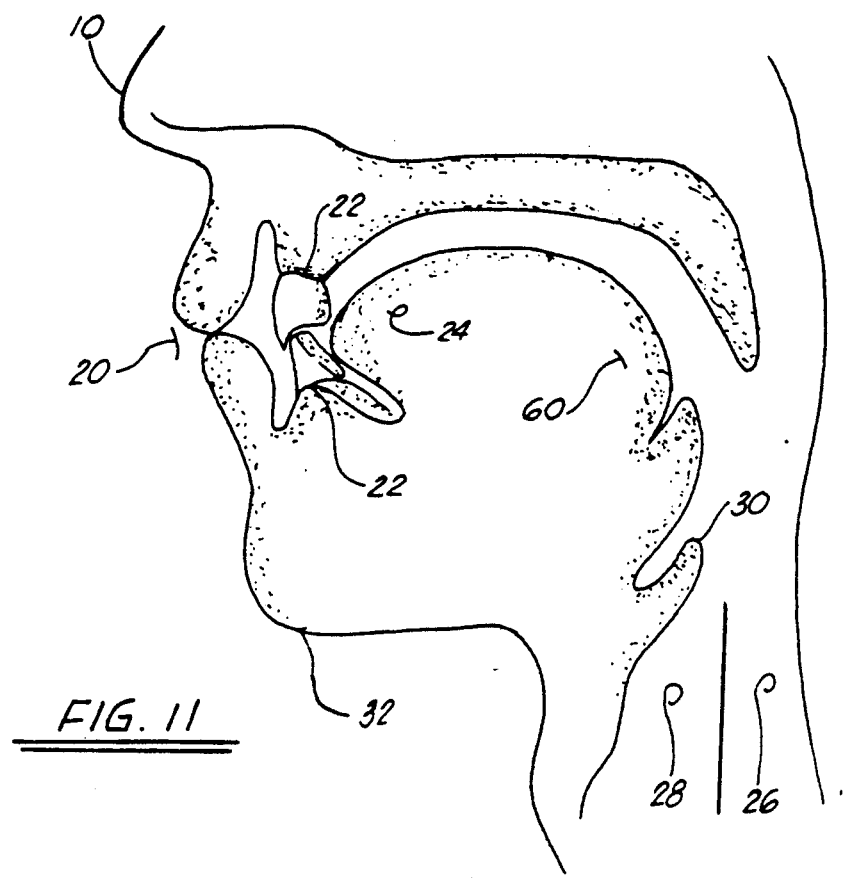
FIG. 11 is a side sectional view of the oral cavity of a non-edentulous human.
Figure 12:
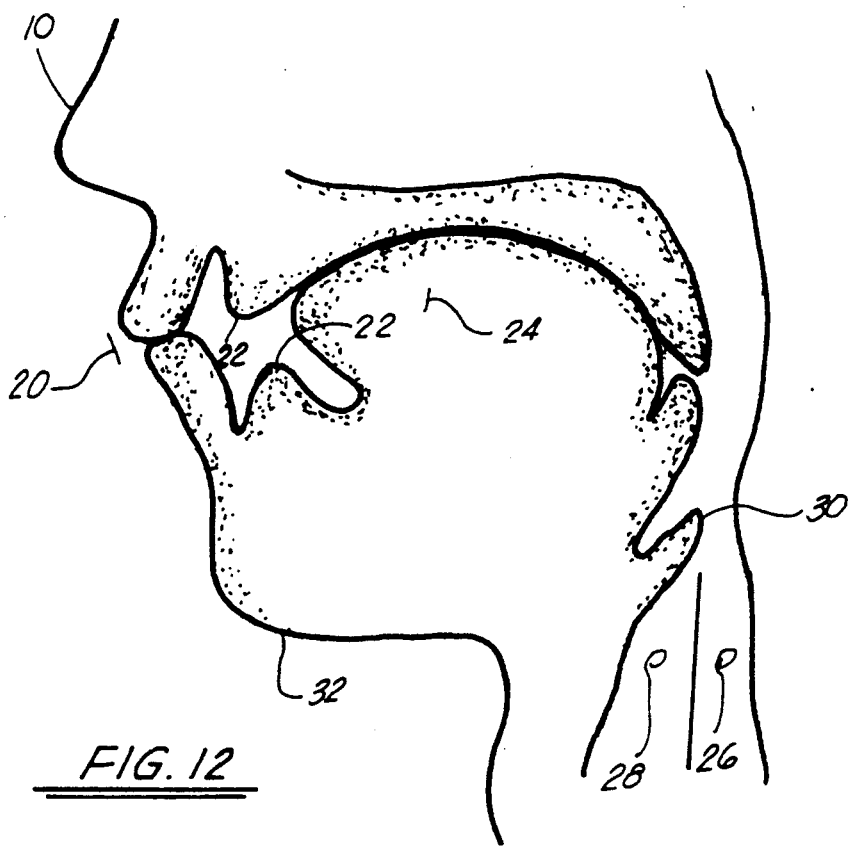
FIG. 12 is a sectional view showing the reduction in the oral cavity in an edentulous human.

Referring to the figures, we show, in side section a typical edentulous individual 10. It is estimated that as much as thirty percent of the elderly population are substantially without teeth.

A normal individual 10 has a facial position determined by the position of the mouth 20. The teeth 21, meeting along their occlusal surface 23 determine the relative positioning of the mandible 32 or lower jaw.

In the normal mouth 20 as positioned by a proper set of teeth 21 a sufficient area 24 exists for the placement of the tongue 25. This placement then properly positions and opens the larynx 26 permitting free passage to either the esophagus 26 or for breathing through the trachea 28.

It is of course well known that the epiglottis 30 is a loose fleshy area behind the tongue 24 which is used to seal the trachea during eating so that food will pass only through the esophagus.

In the edentulous individual 10 where teeth are missing the occlusal surface 23 is defined by the position of the gums 22. Since this is an abnormal condition the normal open tongue area 24 is closed and the mandible 32 moves in a rear position. The epiglottis is then in a position to close off the larynx, sealing the trachea and preventing breathing.

Referring to the skeletal picture, it can be more clearly seen where the temporomandibular joint 40 is activated to position the mandible.

As is known, the temporomandibular joint (TMJ) 40 has both a hinge and a gliding action. It is formed where the condyloid process 36 at the rear of the mandible is suspended, the condyloid head (the superior aspect of the condyle) 38 being positioned within the glenoid fossa 42, supported against friction by a fibrocartilage lining 46 and lubricated by the articular disk 44.

As is known, this is not a mechanically enclosed hinged joint but one rather that is positioned by the musculature reacting on three ligaments, the stylomandibular ligament 50, the temporomandibular ligament 52, and the sphenomandibular ligament 54; this is well known to those of skill in the art and these ligaments are not shown.

The result, however, is that there is no positive bone positioning of the mandible. Normal muscular conditioning of the patient creates a neutral habitular position that is based upon the patient's mandibular position when the patient had teeth. With the loss of teeth with increasing age, there is no mechanical definition within the skeletal structure of a proper jaw position for an individual.

There is, however, a technique, developed in dentistry for the positioning of dentures, the so-called TENS Technique which is designed to detect, by neural stimulation, a neuromuscularly balanced position of the temporomandibular joint by determining a position which essentially is a position of least muscular strain on the ligaments suspending the mandible within the joint.

This technique has been described in the printed literature, including "Neuromuscular Clinical Techniques for Maximum Functional and Aesthetic Rehabilitation of the Edentulous Patient" by Bernard Jankelson and Robert Jankelson, *Myotronics Research, Inc.*, one of a number of published, undated publications by Myotronics Research, Inc. on the TENS Technique.

It has been determined by the inventor that a significant cause of sleep apnea in the edentulous elderly is related to the slack position of the mandible during sleep. In either the mouth closed or the slack jaw position, the mandible is positioned more to the rear than would be the case for an individual with a full set of teeth and with the proper bite pattern; in sleep, with the resulting muscular relaxation, this results in the epiglottis covering the trachea, producing periods of breath deprivation.

It is known that the carbon dioxide cycle of blood determines the frequency of breathing. The cessation of breath in the edentulous elderly builds up the carbon dioxide to the point where, hopefully, a breath is finally forced over the closure of the breathing passageways and the trachea by the epiglottis, which closure is believed to be in large part due to the mispositioning of the mandibular structure. However, while the carbon dioxide level builds up, the blood oxygen level decreases and, significant oxygen deprivation has been reported in patients with continuing sleep apnea.

In turn, this separated pattern of cycles of sleep apnea and oxygen deprivation produce, as is known, a significantly poor pattern of sleep in the elderly patient. This in turn produces major medical problems for such patients. This is documented in the literature; a suitable summary is "*Physicians' Guide to the Recognition and Treatment of Sleep Disorders in the Elderly*", David J. Kupfer, M.D. and Thomas Crook Ph.D., Editor, Mark Poley Associates, Inc., 1984.

It is the discovery of the inventor that, if the mandibular position can be restored during sleep by providing a suitably comfortable set of dental appliances that properly position the mandibular structure, the degree of sleep apnea is significantly reduced.

Normal dentures are almost inevitably removed by the wearer during sleep. This is principally because the typical denture produces a low grade of discomfort in the wearer, not so much from irritation to the gum surfaces which gradually toughen but rather because of muscular fatigue in the neuromuscular structure of the temporomandibular joint due to small levels of mispositioning of the joint.

Therefore, it is the inventor's discovery that if a matching set of dental appliances having comfortable gum covers in the form of a full plate, upper and lower dentures, are provided an edentulous patient, but constructed, in distinction to having a teeth biting surface, with mating upper plate and lower plate occlusal surface defining a specific position and angle in the closed mouth position as will be described below, that this discomfort is alleviated and the incidence of oxygen deprivation in sleep apnea is significantly reduced.

The structure of the dental plates, as shown in the figures, follows in part standard Myotronics prosthetic practice, that is, the nocturnal sleep appliance 70 of the invention is based upon a dental upper and lower dental plate 72. Each of plates 72 is formed on an individual base 74 measured in fit in accordance with, knowledge in the art, to comfortably rest upon the gums, that is upon the residual alveolar ridge 75 in the edentulous patient.

The mating part of the inventive nocturnal appliance, however, comprises two, mating occlusal rests 76, cut as essentially planar surfaces.

The spacing of the occlusal rest 76 defining the occlusal closure position 80 is created by determining, using the TENS Technique a defined neuromuscular balanced position 60 of the temporomandibular joint, the Nocturnal sleep appliances 70 of the invention being in the mouth.

Using much the same technique as is utilized for cutting a bite pattern within a set of dentures, but in a simplified manner because of the nature and construction of the occlusal rests 76 described above, the proper angle and meeting of the occlusal rest surfaces 77 may be readily determined so that the occlusal closure position 80 for a given patient is the neuromuscular balanced position.

This position being determined and the nocturnal sleep appliances being constructed, the edentulous patient may then comfortably wear the same at night during sleep to maintain a proper mandible position.

It is the belief of the inventor that, in addition to the benefits provided by the mechanical positioning of the mandible of the patient during sleep, a significant improvement on sleep may be attributed to the relaxation of the 5th and 7th intercranial nerves, which occurs as a consequence of the maintenance of the neuromuscularly balanced TMJ position.

In a limited number of experimental tests within a sleep laboratory, four patients were tested within a certified sleep laboratory, and were measured for the following criteria:

a. The percentage of sleep time spent in deep restful sleep;
b. The percentage of time spent in rem sleep;
c. The total number of apneic episodes;
d. The oxygen desaturation level;
e. The number of oxygen desaturations; and
f. The apnea index which is considered a guide in terms of the overall number of apneas and deficiency.

|  | Without Orthotic Appliance | With Orthotic Appliance |
| --- | --- | --- |
| % Delta Sleep | 10.5% | 19.3% |
| % REM Sleep | 9.3% | 19.5% |
| Total Sleep Time | 338 minutes | 364 minutes |
| Number of Apnea | 292.5 | 237.3 |
| Number of Desaturation | 101.0 | 18.8 |
| Apnea Index | 52.3 | 37.8 |

It can thus be seen that a significant improvement in the Apnea Index accompanies the use of the orthotic device of the current invention and that even though it has not in all cases totally eliminated apnea, it is capable of reducing apnea in the affected class of individuals.

It can thus be seen that the invention should not be restricted to the exact embodiment described above, but rather extends to that wider range of equivalent devices and processes as are presented in the claims.

I claim:

1. A process for reducing the occurrence of apneic episodes in an edentulous person comprising:

determining a neuromuscularly balanced position of the temporal mandibular joint of the edentulous person;

determining a jaw position and angle of the edentulous person corresponding to said neuromuscularly balanced position, said jaw position and angle being determined relative to the closed mouth position;

shaping an internal two piece oral appliance means to maintain said determined jaw position and angle relative to said closed mouth position; and said person wearing said oral appliance during sleep, the step of shaping said internal appliance further comprising:

shaping an upper and a lower oral plate appliance, said upper appliance and said lower appliance corresponding to said closed mouth position;

facing said upper and said lower appliances with opposing planar rest surfaces;

shaping said opposing planar rest surfaces to maintain, in an opposed juxtaposition, said jaw position and angle relative to said closed mouth position.

* * * * *